United States Patent [19]

Palla et al.

[11] Patent Number: 4,685,954

[45] Date of Patent: Aug. 11, 1987

[54] 3-ACYL SUBSTITUTED OF 2- OR 4-THIAZOLIDINE-CARBOXYLIC ACID HAVING A PHYTO GROWTH REGULATING AND BIOSTIMULATING ACTION

[75] Inventors: Ottorino Palla, Crema; Franco Gozzo, S.Donato Milanese; Marco Radice, Corsico, all of Italy

[73] Assignee: Montedison S.p.A, Milan, Italy

[21] Appl. No.: 886,237

[22] Filed: Jul. 16, 1986

Related U.S. Application Data

[63] Continuation of Ser. No. 713,690, Mar. 19, 1985, abandoned, which is a continuation of Ser. No. 477,441, Mar. 21, 1983, abandoned.

[30] Foreign Application Priority Data

Mar. 22, 1982 [IT] Italy ................................ 20306 A/82

[51] Int. Cl.⁴ ................... C07D 277/06; A01N 43/78

[52] U.S. Cl. .......................................... 71/90; 548/201
[58] Field of Search ............................ 548/201; 71/90

[56] References Cited

U.S. PATENT DOCUMENTS 4,073,918  2/1978  Metz ................................... 514/465

FOREIGN PATENT DOCUMENTS 463144  7/1978  Spain ................................... 514/465

*Primary Examiner*—Robert Gerstl
*Attorney, Agent, or Firm*—Stevens, Davis, Miller & Mosher

[57] ABSTRACT

Derivatives of 2- or 4-thiazolidine-carboxylic acid having an acyl group in position 3 are herein described.

Said compounds are endowed with a phytogrowth regulating and biostimulating action.

2 Claims, No Drawings

3-ACYL SUBSTITUTED OF 2- OR 4-THIAZOLIDINE-CARBOXYLIC ACID HAVING A PHYTO GROWTH REGULATING AND BIOSTIMULATING ACTION

This is a continuation, of application Ser. No. 713,690, filed Mar. 19, 1985 which in turn is a continuation of Ser. No. 477,441 filed Mar. 21, 1983, both now abandoned.

This invention relates to derivatives of 2- or 4-thiazolidine carboxylic acid and more particularly it relates to derivatives of the above-mentioned acids having an acyl group in position 3. This invention relates furthermore to the use thereof as phyto growth regulators and as biostimulants.

An object of the present invention are the compounds of general formula:

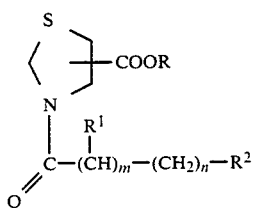

(I)

wherein:
group COOR is in position 2 or 4 in the thiazolidine ring;
R represents a hydrogen atom or an alkyl $C_1$–$C_4$;
$R^1$ represents a hydrogen atom or a methyl;
m is zero or one;
n is zero, one or two;
$R^2$ is naphthyl, indolyl, phenyl or phenoxy, these groups being optionally substituted by 1 to 3 substituents selected from amongst halogen atoms, alkyl or alkoxyalkyl groups $C_1$–$C_4$, phenoxy or pyridyloxy groups, the latter two groups being optionally substituted, in their turn, by 1 to 3 halogen atoms, alkyl or haloalkyl groups $C_1$–$C_4$.

The compounds of formula I are endowed with a phyto growth regulating and biostimulating activity towards useful cultivations in the agrarian field and in floriculture.

Thus, a second object of the present invention resides in the use of the compounds of formula I in the agrarian field and in floriculture as phyto growth regulators and biostimulants.

A third object of this invention is represented by the compositions exerting phyto growth regulating and biostimulating actions and containing, as an active substance, one or more of the compounds of formula I.

The compounds of formula I are prepared by reacting 2-or 4-thiazolidine-carboxylic acid or the respective esters with an acyl halide of formula:

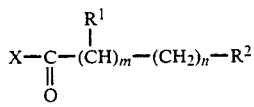

(II)

(wherein X=Cl, Br and $R^1$, $R^2$, m and n have the meaning indicated for formula I).

The reaction is accomplished in an inert solvent and in the presence of a halogenhydric acid-accepting base.

The 2- or 4-thiazolidine-carboxylic acids and the corresponding esters with alcohols $C_1$–$C_4$ are known compounds, the derivatives of 4-thiazolidine-carboxylic acid represent one of the components of biostimulating compositions for agrarian use and the derivatives of 2-thiazolidine-carboxylic acid have been tested in the pharmaceutical field.

The acyl halides of formula II are compounds generally known either as such or in the form of carboxylic acid, from which they are preparable according to conventional techniques.

In the case that the acyl halides of formula II should not be immediately available, they may be substituted, in the reaction illustrated hereinabove, by corresponding anhydrides or mixed anhydrides.

For example, the chloride of indolyl-acetic acid is not a known compound, but from the corresponding acid, known in literature, it is possible to prepare a mixed anhydride by reaction with a suitable acyl halide, e.g. sec.butyl-chloroformiate, and the resulting mixed anhydride is properly suited to the synthesis of the compounds of formula I.

Comprised in general formula I are the compounds in which the substituent on the nitrogen atom derives from benzoic acid, 2-phenyl- or 2-phenoxy-propionic acid, phenyl-acetic acid, phenoxyacetic acid, naphthyl-acetic acid, indolyl-acetic acid, 4- indolyl-pentanoic acid etc., these acyls being optionally substituted.

Furthermore, examples of compounds of formula I are the derivatives of 2-thiazolidine-carboxylic acid of formula:

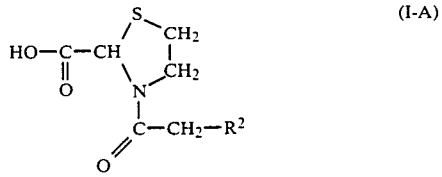

(I-A)

wherein $R^2$ may be: α-naphthyl; β-naphthyl; 3-indolyl; phenyl; phenoxy; 2-chlorophenoxy; 2,4-dichlorophenoxy; 4-chlorophenoxy; 2-meyhyl-4-chlorophenoxy; 2-methoxy-4-chloro-phenoxy; 4-phenoxyphenoxy; 3- phenoxy-phenoxy; 3(or 4)-[2,4-dichlorophenoxy]-phenoxy; 3(or 4)-[2-methyl-4-chloro-phenoxy]-phenoxy; 2-chloro-pyridyloxy; 2,4-dichloropyridyloxy; 3-phenoxy-pyridyloxy; 4-pyridyloxyphenoxy; and the corresponding esters with alcohols $C_1$–$C_4$.

Further examples of compounds of formula I are the derivatives of 4-thiazolidine-carboxylic acid having formula:

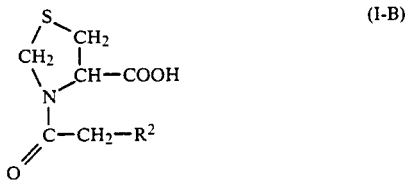

(I-B)

(wherein $R^2$ has the same meanings as specified for formula I-A) and the respective esters with alcohols $C_1$–$C_4$.

Some of the compounds of formula I, depending on how they were prepared, may be in the form of salts.

Both the compounds of formula I as such, and the corresponding salts fall within the scope of the present invention.

The compounds of formula I are endowed with interesting biological properties as they posses a hormone-like activity as growth regulators (phyto growth regulators) and as biostimulants.

As far as we know, these properties are not necessarily related with each other, as no compounds associating these properties are known from the literature.

Conversely, as regards the compounds forming an object of this invention, it can be stated that they combine the phyto-growth regulating properties with the biostimulating properties, although within the same class there are compounds in which a certain activity is prevailing over the other; however, this is a normal fact as regards the compounds endowed with a biological activity, since, within the same class, there are compounds endowed with a qualitatively or quantitatively different biological activity.

The phyto growth regulating activity of the compounds of formula I results in an interference in the action of the endogenous hormones of the plant, while maintaining unaltered the vital functions of the plant.

The compounds of the invention, for example, have the characteristic of preventing or annulling the action of the auxinic hormones both of natural origin (indolacetic acid) and of synthetic origin (e.g. 2,4-dichloro-phenoxyacetic acid, common name 2,4-D).

As is known, the synthetic auxines, such as e.g. 2,4-D, may cause alterations to the plant metabolism.

These alterations cause, at sufficiently high doses of synthetic auxine, an abnormal development of the plant, which may lead to the death of the plant.

In fact, 2,4-D is diffusely used as a herbicide in spite of the fact that such application requires particular measures in order not to damage the useful cultivations.

When this synthetic auxin is employed in admixture with the compounds of formula I, there is a reduction in the plant growth practically similar to the one obtainable by using only the compound of formula I in the same dose.

As a consequence thereof, the effect of the synthetic auxin is even annulled. Analogous effects, although less remarked, were observed on natural auxine (indolacetic acid).

This property of the compounds of formula I opens interesting prospects to the protection of useful cultivations from the damages caused by herbicides of the auxinic type.

Moreover, the compounds of formula I are employable also as antidotes in the protection of cultivations of agrarian interest from the toxic action exerted by non-selective herbicides.

The compounds of formula I, when utilized as phyto growth regulators, are preferably applicated to the plant leaves, or to the seeds by tanning.

The compounds of formula I are preferably utilized in the form of proper compositions.

Said compositions, according to the usual formulating practice, may contain, besides the active compound of formula I, also solid or liquid inert vehicles and optionally other additives commonly used, such as surfactants, wetting agents, dispersants and adhesion-promoting agents.

The amount of compound of formula I to be distributed for the use as phyto growth regulator varies as a function of various factors, such as type of cultivation, type of composition, climatic and environmental factors.

Generally, amounts ranging from 0.01 to 1 Kg/ha are sufficient to achieve the desired phyto growth regulating effect.

As concerns the biostimulating action of the compounds of formula I, such action is, in some cases, decidedly high and superior to the one of known biostimulants such as naphthalene-acetic acid.

The effect of the compounds of formula I results in a more luxuriant appearance of the plant and in an increase in the fruit harvest.

The compounds of formula I, when utilized as biostimulants, can be applied either to the plant or to the seeds or also in the medium in which the plant grows.

In order to get a better distribution of the product it is generally preferable to use the compounds of formula I in the form of suitable compositions which, according to the usual formulating practice, contain also solid or liquid inert vehicles and optionally other usual additives such as e.g. surfactants, wetting agents, adhesion-promoting agents and dispersants.

The applicative field of the compounds of formula I as biostimulants covers the cultivations of agrarian interest such as cereals, horticultural cultivations, fruit-trees and ornamental plant cultivation.

The compound amount to be distributed for the use as a biostimulant varies as a function of various factors such as type of cultivation, composition employed, climatic and environmental conditions. Generally, amounts ranging from 0.01 to 1 Kg/ha are sufficient to achieve the desired biostimulating effect.

The following examples are given to better illustrate the present invention.

EXAMPLE 1

Preparation of N-(2-methyl-4-chloro-phenoxyacetyl)-2-thiazolidine-carboxylic acid (Compound No. 1)

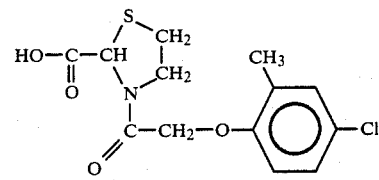

1.38 g (0.01 moles) of K$_2$CO$_3$ were added under stirring to a biphase system consisting of:

a solution of 2-thiazolidine-carboxylic acid (1.35 g; 0.01 moles) in water (3 ml), a solution of 2-methyl-4-chloro-phenoxyacetyl-chloride (2.2 g; 0.01 moles) in methylene chloride (10 ml).

The resulting mixture was stirred at room temperature for two hours after conclusion of the addition.

The two phases were then separated. The aqueous phase was brought to an acid pH and was extracted with ethyl acetate.

The organic phases were dried and the solvent was removed by evaporation under reduced pressure.

1.9 g of the desired product in the form of a thick, slowly solidifying oil were thus obtained.

A sample crystallized from toluene exhibited a melting point of 147°–148° C. (NMR consistent with the assigned structure).

EXAMPLE 2

Preparation of N-(3-indolyl-acetyl)-4-thiazolidine-carboxylic acid (Compound No. 2)

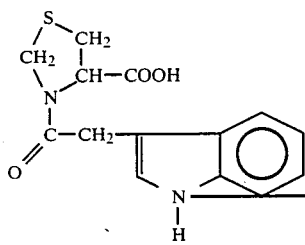

To a solution of 3-indolacetic acid (1.75 g; 0.01 moles) and triethylamine (1 g; 0.01 moles) in anhydrous dimethylformamide (40 ml) maintained under stirring at 0° C. there were added dropwise 1.36 g (0.01 moles) of sec.butyl-chloroformiate $$(Cl-\underset{\underset{O}{\|}}{C}-O-\underset{\underset{CH_3}{|}}{CH}-CH_2-CH_3).$$

At the conclusion of the addition, the temperature was allowed to rise to the room temperature value, and 1.33 g (0.01 moles) of 4-thiazolidine-carboxylic acid were added. The reaction mixture was heated to 40° C. for 2 hours, then is was concentrated, and 100 ml of water were added thereto.

It was then extracted with ethyl acetate. The joined organic phases were dried and the solvent was evaporated by distillation under reduced pressure.

There were obtained 1.5 g of a rough product (oil), which was purified by chromatography on silica gel (eluent: hexane-ethyl acetate in a ratio of 1:9). Thus there were obtained 0.5 g of the desired product in the form of a crystalline solid (melting point = 166°-167° C.) crystallized from ethanol at 95% (IR consistent with the assigned structure).

EXAMPLE 3

Compounds according to the present invention prepared starting from the proper acyl chloride and from 2- or 4-thiazolidine-carboxylic acid or esters thereof and by operating in like manner as described for the preparation of compound No. 1 (example 1) are indicated in following Table 1. Exception is made for the preparation of compound No. 2, which is described in example 2.

TABLE 1

Compounds of formula (1)

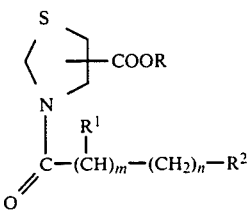

| Compound No. | Position of group COOR | R | m | $R^1$ | n | $R^2$ | m.p.[2] (°C.) | IR[3] (cm$^{-1}$) |
|---|---|---|---|---|---|---|---|---|
| 1 | 2 | H | 1 | H | O | 2-methyl-4-chloro-phenoxy | 147–148 | 1735, 1640 |
| 2 | 4 | H | 1 | H | O | 3-indolyl | 166–167 | 1710, 1625[4] |
| 3 | 4 | H | 1 | H | O | 1-naphthyl | 149–150 | 1735, 1615 |
| 4 | 2 | H | 1 | H | O | 1-naphthyl | 194–195 | 1710, 1655 |
| 5 | 4 | $CH_3$ | 1 | H | O | 1-naphthyl | 105–106 | 1740, 1630 |
| 6 | 2 | $CH_3$ | 1 | H | O | 2-methyl-4-chloro-phenoxy | oil | 1740, 1670 |
| 7 | 4 | $CH_3$ | 1 | H | O | 2-methyl-4-chloro-phenoxy | oil | 1738, 1670 |
| 8 | 4 | $CH_3$ | 1 | H | O | 4-chloro-phenoxy | 58–60 | 1740, 1660 |
| 9 | 4 | $CH_3$ | 1 | H | O | 2,4-dichloro-phenoxy | oil | 1740, 1665 |
| 10 | 2 | H | 1 | H | O | 2,4-dichloro-phenoxy | 129–130 | 1720, 1640 |

Notes to Table 1
[1]The elemental analysis of all the compounds was consistent with the assigned structure.
[2]The melting points were not corrected.
[3]There are recorded, in the order, the bands corresponding to $\nu COOR$ and $\nu CO-N$.
[4]$\nu N-H$ at 3225 cm$^{-1}$.

EXAMPLE 4

Phyto growth regulating activity

Pea internode lengthening test.

General modalities: Pea seeds (Alaska cv.) were soaked for 3 hours in running water, whereafter they were sowed into moist sawdust, in darkness, in a conditioned room from at 25° C. and at 80% of relative humidity. After an eight-day growth, a 5 mm long segment was cut from the second internode of each plant.

The segments so obtained were left 30 minutes in a $5.10^{-4}$ molar solution of calcium sulphate, then they were transferred into the solutions containing the substance to be tested.

Each sample consisted of 30 segments immersed in 5 ml of test solution.

The test solutions consisted in a $5.10^{-4}$ molar solution of calcium sulphate in which a predetermined amount of the compound to be tested was dissolved (pH = about 5.7).

As a check, plant segments were kept under the same conditions in a $5.10^{-4}$ molar solution of calcium sulphate without any other compounds.

The samples were kept in a thermoregulated "Dubnoff" bath at 25° C. for a time of 4 hours.

At the end of such time period, the samples were taken out from the test solution and the length of the segments was measured.

The compound activity was determined by measuring the lengthening of the treated segments in comparison with the lengthening of the check segments, indicating the latter with 100.

Compounds of this invention showed an inhibiting activity towards the pea internode lengthening.

For comparative purposes, also the activity of known auxinic phyto growth regulators and the activity of mixtures of compounds of the invention with the known auxinic phyto growth regulators were tested.

The results of these comparative tests showed that the phyto growth regulating activity of compounds of the present invention inhibited or annulled that of the auxinic phyto growth regulators.

TABLE 2

Phyto growth regulating activity, pea internode lengthening test.

| Compound[1] | Molar concentration in the test solution | Average lengthening |
|---|---|---|
| Check | — | 100 |
| N° 4 | $10^{-3}$ | 40 |
|  | $10^{-4}$ | 40–70 |
| N° 9 | $10^{-3}$ | 53 |
| 2,4 - D | $10^{-4}$ | 250 |
|  | $10^{-6}$ | 250 |
| IAA | $10^{-6}$ | 275 |
| N°4 + IAA | $10^{-3}$(N° 4) + $10^{-6}$(IAA) | 150 |
| N°9 + 2,4 D | $10^{-3}$(N°4) + $10^{-6}$(2,4-D) | 53 |
| N°9 + IAA | $10^{-3}$(N°9) + $10^{-6}$(IAA) | 113 |

Notes to Table 2
[1]Compounds Nos. 4 and 9 are described in Table 1 IAA = indolacetic acid (natural auxin); 2,4-D = 2,4-dichloro-phenoxyacetic acid (herbicide with auxinic activity).

EXAMPLE 5

Phyto growth regulating activity

Oats coleoptile lengthening test.

General modalities: oats seeds (Sole cv.) were soaked in running water for 3 hours and then sowed into wet poplar sawdust, whereafter they were allowed to sprout in darkness in a conditioned environment at 25° C. and at 80% of relative humidity.

As the coleoptiles reached a 3–4 cm length (in about 3–4 days), a 5 mm segment was cut from each of them. The first 2 mm of apex were excluded from the cut.

The segments so obtained were left for 30 minutes in a $5.10^{-4}$ molar solution of calcium sulphate, whereupon they were transferred into the solution containing the compound being tested. Each sample consisted of 30 segments immersed in 5 ml of test solution consisting of a $5.10^{-4}$ molar solution of calcium sulphate, in which the predetermined amount of compound to be tested was dissolved.

The samples were kept in a thermoregulated "Dubnoff" bath at 26° C. for a 4-hour time period.

As a check, cut segments were kept under the same conditions in a solution containing only calcium sulphate.

At the conclusion of said period, the samples were taken from the test solution and the length of each segment was measured.

The phyto growth regulating activity of the compounds was determined by measuring the lengthening of the treated samples in respect of the check, indicating the latter with 100.

Compounds of the invention exhibited a phyto growth regulating activity by inhibiting the lengthening of the oats coleoptiles.

The results are recorded on following Table 3.

TABLE 3

Phyto growth regulating activity, oats coleoptile lengthening test.

| Compound[1] | Molar concentration in the test solution | Average lengthening |
|---|---|---|
| No. 9 | $10^{-3}$ | 43 |
| 2,4-D | $10^{-4}$ | 293 |
| Check | — | 100 |

Notes to Table 3
[1]Compound No. 9 is described in Table 1; 2,4-D: 2,4-dichloro-phenoxyacetic acid (weed-killer with auxinic activity).

EXAMPLE 6

Biostimulating activity on strawberry cultivation (Pocaleontas cv.) in natural conditions by application onto the leaves General modalities: there were prepared aqueous solutions of the products being tested at the desired concentration in water containing 0.1% of "Emulson 20 OM" (registered trade-mark of ROL Co. for sorbitan-oleate-polyethoxylate containing 20 moles of ethylene oxide per mole of substrate).

A strawberry field was suitably divided into lots and the various lots were treated by sprinkling with the test solutions. As a check, other lots were sprayed with an equal amount of aqueous solution at 0.1% of "Emulson 20 OM" without any other products.

The treatment was repeated three times in the period from the beginning to the end of blossoming.

The biostimulating activity was determined by comparing the weight of the fruits produced in the treated lots with the weight of the fruits produced in the check lots.

The results recorded in following Table 4 clearly indicate that the compounds of the invention possess a biostimulating activity as they are capable of increasing the strawberry crop.

Their biostimulating activity, furthermore, results to be higher than the one exerted by naphthalene-acetic acid, a known biostimulant.

TABLE 4

| Biostimulating activity on strawberry. | | | |
|---|---|---|---|
| Compound[a] | Molar concentration in applicated solution | Production (g/ha) | Increase (%) |
| Check | — | 220.6 | — |
| No. 3 | $2.10^{-4}$ | 238.4 | 8.1 |
| No. 4 | $2.10^{-4}$ | 257.8 | 16.9 |
| ANA | $10^{-4}$[b] | 232.6 | 5.4 |

Notes to Table 4
[a]Compounds Nos. 3 and 4 are described in Table 1; ANA = α-naphthalene-acetic acid (commercial biostimulant).
[b]Utilization dose suggested for naphthalene-acetic acid. At higher doses, epinastic effects (alterations in the orientation of the leaves) are observed.

What we claim is:
1. A compound of formula:

$$\text{(I)}$$

in which:
R is a hydrogen atom or a $C_1$–$C_4$ alkyl; and $R^2$ is a 1-naphthyl or 3-indolyl radical, said compound being characterized in that it is useful in agriculture and floriculture as both a phyto-growth regulator and a biostimulant.

2. The method of regulating the phyto-growth and biostimulating growing agricultural and floricultural plants which consists in treating such plants with an effective amount of at least one compound of formula:

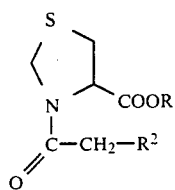
(I)

in which:

R is a hydrogen atom or a $C_1$–$C_4$ alkyl; and $R^2$ is selected from the group consisting of naphthyl, indolyl and phenoxy groups, said groups being substituted by 1 to 3 substituents selected from the group consisting of halogen atoms, $C_1$–$C_4$ alkyl, $C_1$–$C_4$ alkoxy, the phenoxy groups, and the pyridyloxy group, the two latter groups substituted by substituents selected from the group consisting of 1 to 3 halogen atoms, $C_1$–$C_4$ alkyl groups, and $C_1$–$C_4$ haloalkyl groups.

* * * * *

UNITED STATES PATENT AND TRADEMARK OFFICE
CERTIFICATE OF CORRECTION

PATENT NO. : 4,685,954
DATED : August 11, 1987
INVENTOR(S) : PALLA et al.

It is certified that error appears in the above-identified patent and that said Letters Patent is hereby corrected as shown below:

In the Heading of the patent please correct the following error:

[63] --Continuation of Ser. No. 713,690, Mar. 19, 1985, now U.S. Patent No. 4,655,818 dated April 7, 1987, which is a Continuation of Ser. No. 477,441 Mar. 21, 1983, abandoned.--

Signed and Sealed this

Twelfth Day of April, 1988

Attest:

DONALD J. QUIGG

Attesting Officer

Commissioner of Patents and Trademarks